United States Patent [19]
Strubbe et al.

[11] 3,956,314
[45] May 11, 1976

[54] DERIVATIVES OF 2-PYRROLIDINONE

[75] Inventors: Joseph Honoré Strubbe, Dilbeek; Raymond Armand Linz, Brussels, both of Belgium

[73] Assignee: U.C.B., Societe Anonyme, Saint-Gilles-lez-Bruxelles, Belgium

[22] Filed: Nov. 20, 1973

[21] Appl. No.: 417,528

Related U.S. Application Data

[63] Continuation-in-part of Ser. No. 165,342, July 22, 1971, abandoned.

[30] Foreign Application Priority Data

July 24, 1970 United Kingdom............... 35948/70

[52] U.S. Cl.......................... 260/326.5 FL; 424/274
[51] Int. Cl.².......................................... C07D 207/26
[58] Field of Search ........................... 260/326.5 FL

[56] References Cited
UNITED STATES PATENTS

| | | | |
|---|---|---|---|
| 3,471,548 | 10/1969 | Keberle et al. ..................... | 260/471 |
| 3,804,854 | 4/1974 | Loev .......................... | 260/326.5 FL |

OTHER PUBLICATIONS
Strubbe et al., Chem. Abs., Vol. 76:113055j (1972).

*Primary Examiner*—R. Gallagher
*Assistant Examiner*—Mark L. Berch
*Attorney, Agent, or Firm*—Wenderoth, Lind & Ponack

[57] ABSTRACT

Phenyl-2-pyrrolidinones of the formula

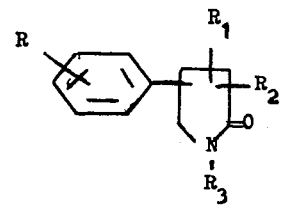

wherein R is a halogen or trifluoromethyl, $R_1$ is lower alkyl, lower alkenyl, lower alkynyl, phenyl or halogen-substituted phenyl, $R_2$ is hydrogen, lower alkyl or phenyl and $R_3$ is hydrogen, lower alkyl, lower alkenyl, lower alkynyl, cyclopentyl or benzyl, as well as the cis and trans diastereoisomers thereof, are active on the central nervous system. In particular they have valuable anxiolytic and antidepressive properties. Processes for their preparation are given.

11 Claims, No Drawings

DERIVATIVES OF 2-PYRROLIDINONE

This application is a continuation-in-part of copending application Ser. No. 165,342 filed on July 22, 1971, now abandoned.

The present invention relates to new derivatives of 2-pyrrolidinone. It relates also to therapeutic compositions containing said new derivatives and to the use thereof in the therapeutic field, more particularly as an anxiolytic drug.

The new compounds according to the present invention are substituted phenyl-2-pyrrolidinones of the formula

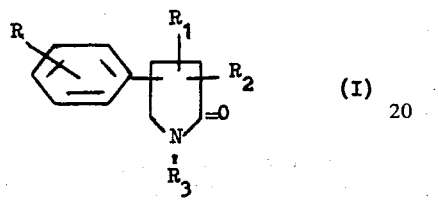

wherein
R is a halogen atom, for example a fluorine, chlorine or bromine atom, or a trifluoromethyl radical;
$R_1$ is an alkyl, alkenyl or alkynyl radical having up to 5 carbon atoms, a phenyl radical or a ring-substituted derivative thereof in which said ring-substituent is a halogen atom,
$R_2$ is a hydrogen atom or an alkyl radical having 1 to 5 carbon atoms, or a phenyl radical, and
$R_3$ is a hydrogen atom, an alkyl, alkenyl or alkynyl radical having up to 7 carbon atoms or a cycopentyl or benzyl radical
and the cis and trans diastereoisomers thereof.

A particularly preferred group constitutes those compounds wherein the R-phenyl radical is attached to the 4-position of the pyrrolidine ring and the $R_1$ radical is attached in the 3-position of the pyrrolidine ring.

We have found that the substituted phenyl-2-pyrrolidinones of the above general formula I possess very interesting therapeutic properties; in particular, they have a considerable action on the central nervous system. For example, they have a marked anxiolytic action, which has been demonstrated by pharmacological tests. Moreover, we have found that they have psychostimulant or antidepressant properties and a protective effect against anoxic anoxia. From this latter property it can be concluded that these substances are useful, for example, in the treatment of the sequelae of cerebrovascular insufficiencies, cranial traumata, and the like. These substances have, in addition, a low toxicity.

The compounds of the present invention can be produced by the methods which are known for obtaining 2-pyrrolidinones, for example, by one of the following processes:

a. cyclization of a 4-amino-butyric acid or of an alkyl ester thereof of the general formula $H(R_3)N$—A—COOX, wherein X is a hydrogen atom of a lower alkyl radical and A a trimethylene chain substituted by R -phenyl, $R_1$ and $R_2$ radicals; R, $R_1$, $R_2$ and $R_3$ having the meanings given above. The 4-amino-butyric acid or the alkyl esters thereof used as starting material can be prepared, for example:

by subjecting an appropriate 3-cyanopropionic acid or an alkyl ester thereof to catalytic hydrogenation;

by subjecting an appropriate 4-nitrobutyric acid or an alkyl ester thereof to catalytic reduction;

by condensing an appropriate 4-oxo-butyric acid with ammonia or a primary amine of the formula $R_3NH_2$, followed by catalytic hydrogenation of the Schiff's base obtained;

by the condensation of an appropriate 4-oxo-butyric acid with hydroxylamine and catalytic reduction of the resulting oxime.

These reductions or hydrogenations can be performed, for example, by reaction with hydrogen under pressure in the presence of palladium on carbon or of Raney nickel or cobalt as catalyst.

by reaction of an alkali metal derivative of an alkyl 2-[R-phenyl]-2-$R_1$-acetate of the formula:

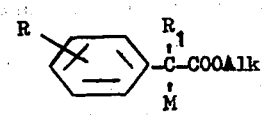

wherein Alk is a lower alkyl radical, M is an alkali metal atom and R and $R_1$ have the meanings given above, with an ethylene-imine of the formula

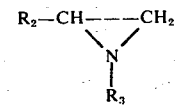

wherein $R_2$ and $R_3$ have the meanings given above.

The 4-amino-butyric acid or the alkyl esters thereof used as starting material can be prepared separately, optionally isolated and then subjected to cyclization; however, the starting material can also be prepared in situ, starting with the materials mentioned above, and cyclized directly, without isolating, to give a 2-pyrrolidinone according to the present invention.

b. hydrolysis of a 2-imino-pyrrolidine of the general formula:

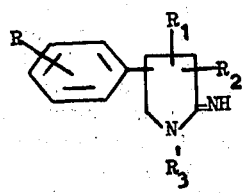

wherein R, $R_1$, $R_2$ and $R_3$ have the meanings given above;

c. reaction, at elevated temperature, of a lactone of the general formula:

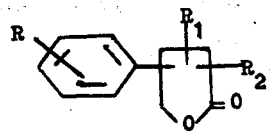

wherein R, $R_1$ and $R_2$ have the meanings given above, with ammonia or a primary amine of general formula $R_3NH_2$, wherein $R_3$ has the same meaning as above;

d. cyclization, in the presence of an alkaline condensation agent, of a 4-halogeno-butyramide of the general formula Hal-A-CONH($R_3$), wherein Hal is a halogen atom and A a trimethylene chain substituted by R-phenyl, $R_1$ and $R_2$ radicals; R, $R_1$, $R_2$ and $R_3$ having the meanings given above;

e. decarboxylation, by heating, of a 2-pyrrolidinone-3-carboxylic acid of the general formula:

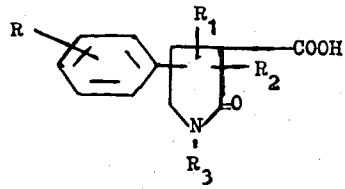

wherein R, $R_1$, $R_2$ and $R_3$ have the same meanings as above.

In order to prepare substituted phenyl-2-pyrrolidinones of the general formula (I) in which $R_3$ is not a hydrogen atom, i.e. phenyl-2-pyrrolidinones substituted on the nitrogen atom, it is also possible, in accordance with conventional methods, to introduce a substituent on the cyclic nitrogen atom of a corresponding phenyl-2-pyrrolidinone in which the nitrogen atom is not substituted and which has been obtained by one of the methods (a) to (e) above. Thus, it is possible, for example, to react an appropriate phenyl-2-pyrrolidinone with an $R_3$ halide in the presence of an alkaline condensation agent, $R_3$ being an alkyl, alkenyl or alkynyl radical having up to 7 carbon atoms or a cyclopentyl or benzyl radical.

In the particular case of substituted phenyl-2-pyrrolidinones of the general formula (I) in which R is a halogen atom in the para-position, it is also possible to proceed in the following manner: an appropriate substituted phenyl-2-pyrrolidinone, the phenyl radical of which is not substituted, is nitrated by means of nitric acid, a mixture of concentrated nitric and sulfuric acids or some other appropriate nitration agent, for example, in order to obtain the corresponding substituted p-nitro-phenyl-2-pyrrolidinone. This nitro derivative is then subjected to catalytic or chemical reduction and converted into the corresponding substituted p-aminophenyl-2-pyrrolidinone. Finally, this amino derivative is subjected to diazotization in an aqueous medium with an alkali metal nitrite in the presence of a halohydric acid at a temperature of 0°–5°C. in order to obtain the corresponding diazonium salt, and this salt is subjected to a Sandmeyer reaction in the presence of a cuprous halide or copper powder to give the corresponding substituted p-halophenyl-2-pyrrolidinone (R = halogen). These different reactions can be represented by the following equations:

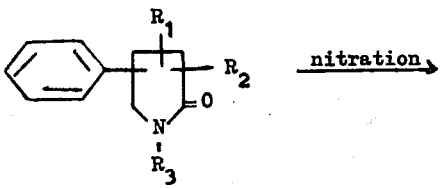

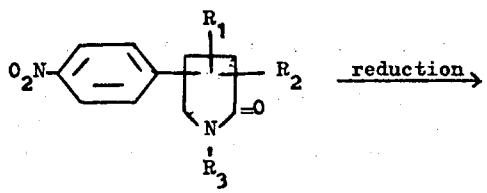

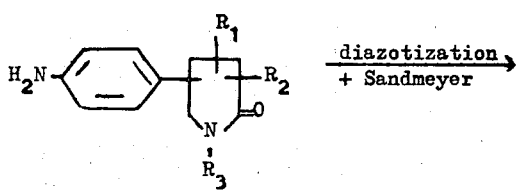

wherein Hal is a halogen atom and $R_1$, $R_2$ and $R_3$ have the same meanings as above.

The phenyl-2-pyrrolidinones prepared by the foregoing methods are often obtained in the form of mixtures of the cis and trans diastereoisomers. These mixtures can be separated into their cis and trans components by known methods, for example by fractional crystallization or by column chromatography. Furthermore, the products may consist of racemic mixtures of optically-active isomers. Such mixtures can also be separated into their optical antipodes in the usual manner.

Thus, the present invention also comprises the cis and trans diastereoisomers and the optically-active isomers and racemic forms of the substituted phenyl-pyrrolidinones of general formula (I).

To demonstrate the anxiolytic action of the compounds according to the present invention the following test was performed.

Wistar rats (weighing 100 g. ± 20 g.) are first permitted to become accustomed, during 10 minutes, to conditioning cages of the shuttle box type, after which they are subjected to a first sequence of 20 painful electric shocks of 3 seconds on their paws repeated every 30 seconds. During this first sequence, the rats ran away before the end of the shock about 15 times out of 20 shocks.

On the other hand, if these same animals are subjected to a sequence of shocks 4 hours later, paradoxically, instead of improving their performance (as in the course of a normal training) a reduction in the number of evasions is found: the animals have become set and are less successful in running away before the end of the shocks. This behavior is attributed to an anxiety state induced by the experimental situation.

Intraperitoneal administration of an anxiolytic substance to the rats, half an hour before the second sequence is carried out, improves their performance (increase in the number of evasions before the end of the shock).

A group of rats, to which a substance to be tested is administered, is compared with a group of control rats, which has been injected with physiological serum under the same conditions.

The activity of a substance tested is expressed by the difference between the number of evasions found in the group of rats, to which a substance to be tested has been administered, and the number of evasions found in the group of control rats, during the second sequence of shocks. Generally, a mean decrease of 4 evasions is found per group of 20 control rats during the second sequence. The compounds tested, which increase the number of evasions found in the control rats by at least 3 evasions, are considered as having an anxiolytic activity. Those compounds, which increase the number of evasions found in the control rats by 2 evasions are potentially active. Those compounds, which increase the number of evasions found in the control rats by less than 2 are considered inactive.

In the test the minimum dose is sought which increases the performances of the rats treated in comparison with with the control rats.

The following compounds, designated with the letters A to T, were subjected to this test.

A. 4-p-chlorophenyl-3-ethyl-2-pyrrolidinone (cis isomer)

B. 4-p-chlorophenyl-3-ethyl-2-pyrrolidinone (trans isomer)

C. 4-p-chlorophenyl-3-methyl-2-pyrrolidinone (cis isomer)

D. 4-p-chlorophenyl-3-methyl-2-pyrrolidinone (trans isomer)

E. 4-p-chlorophenyl-3-phenyl-2-pyrrolidinone (cis isomer)

F. 4-p-chlorophenyl-3-phenyl-2-pyrrolidinone (trans isomer)

G. 4-o-chlorophenyl-3-phenyl-2-pyrrolidinone

H. 4-p-fluorophenyl-3-methyl-2-pyrrolidinone

I. 4-p-chlorophenyl-N-methyl-3-phenyl-2-pyrrolidinone

J. 4-p-fluorophenyl-3-phenyl-2-pyrrolidinone

K. 3-o-chlorophenyl-4-p-chlorophenyl-2-pyrrolidinone

L. 4-p-chlorophenyl-4-phenyl-2-pyrrolidinone

M. N-benzyl-4-p-chlorophenyl-3-phenyl-2-pyrrolidinone

N. 4-p-chlorophenyl-5-ethyl-3-phenyl-2-pyrrolidinone

O. 4-p-chlorophenyl-3-phenyl-N-(2-propynyl)-2-pyrrolidinone

P. 4-p-chlorophenyl-N-cyclopentyl-3-phenyl-2-pyrrolidinone

Q. 3-allyl-3-p-chlorophenyl-5-phenyl-2-pyrrolidinone (isomer of m.p. 197°–198°C.)

R. 3-phenyl-4-m-trifluoromethylphenyl-2-pyrrolidinone.

S. chlordiazepoxide or 7-chloro-2-methylamino-5-phenyl-3H-1,4-benzodiazepine-4-oxide.

T. 4-(para-chlorophenyl)-pyrrolidone-(2).

Compounds A to R are compounds according to the present invention, whereas compounds S i.e. chlordiazepoxide is a well known anxiolytic drug and compound T is a known compound most nearly comparable to the pyrrolidinones of Formula (I) (see Example 2 of U.S. Pat. No. 3,471,548). In the following Table there is shown in the first column the compound tested; in the second column, the dose administered (in mole per kg animal body weight) and in the third column the improvement in the performance (i.e. the difference between the number of evasions found in the treated rats and the number of evasions found in the control rats during the second sequence of shocks).

| Compound | Dose | Improvement in the performance |
|---|---|---|
| A | 0.10 | +3 |
| B | 0.10 | +2 |

-continued

| Compound | Dose | Improvement in the performance |
|---|---|---|
| C | 0.10 | +5 |
| D | 0.056 | +3 |
| E | 0.018 | +4 |
| F | 0.01 | +2 |
| G | 0.056 | +3 |
| H | 0.10 | +2 |
| I | 0.0056 | +3 |
| J | 0.032 | +6 |
| K | 0.0075 | +4 |
| L | 0.10 | +2 |
| M | 0.10 | +2 |
| N | 0.032 | +5 |
| O | 0.018 | +4 |
| P | 0.10 | +3 |
| Q | 0.032 | +3 |
| R | 0.10 | +4 |
| S | 0.01 | +3 |
| T | 0.10 | −2 |
| T | 0.32 | −2 |

As apparent from the foregoing Table, the compounds according to the present invention show a significant anxiolytic action (increase in the number of evasions found in the control rats by at least three), whereas the already known compound T most nearly comparable to the pyrrolidinones of Formula (I) possess practically no anxiolytic action (a decrease in the performance is found even at a dose of 0.32 mmole/kg).

Moreover, the compounds of the invention have low toxicity. Thus, the toxicity determined in rat by intraperitoneal administration ($LD_{50}$) is 306 mg./kg. for compound D and 320 mg./kg. for compound E, whereas for chlordiazepoxide it is 240 mg/kg. mode The compounds described herein may be administered orally, in the form of solid or liquid compositions comprising the usual excipients, or rectally, in the form of suppositories. In general, they are administered at doses of from 20 to 200 mg of the active principle once or twice per day, although variations occur depending on the weight and state of health of the subject to be treated as well as the particular moe of administration chosen.

The following Examples are given for the purpose of illustrating the present invention:

EXAMPLE 1

4-p-chlorophenyl-3-phenyl-2-pyrrolidinone 30 g. of ethyl 4-amino-3-p-chlorophenyl-2-phenyl-butyrate are heated for 15 minutes at 150°C. Liberation of ethanol is observed. The reaction medium is taken up in 120 ml. of toluene and the resulting solution is filered. After cooling the solution, the crystals formed are separated and recrystallized several times from toluene. 12 g. of 4-p-chlorophenyl-3-phenyl-2-pyrrolidinone are obtained; m.p. 148°–151°C. Nuclear magnetic resonance analysis shows that it is the cis-isomer.

By concentration and fractional crystallization of the mother liquor, a small quantity of the trans-isomer is obtained; m.p. 130°–135°C.

The ethyl 4-amino-3-p-chlorophenyl-2-phenyl-butyrate used as starting material is prepared in the following way:

To 20 g. of ethyl 3-p-chlorophenyl-3-cyano-2-phenyl-propionate in 500 ml. ethanol, there is added an equimolar solution of hydrochloric acid in ethanol. The resulting solution is hydrogenated in a Parr bomb with hydrogen at a pressure of 4 kg./cm.² in the presence of 1.5 g. of palladium on carbon (5%) at a temperature of about 40°–50°C. until about 90% of the theoretical quantity of hydrogen has been absorbed (to prevent hydrogenolysis of the chlorine) i.e. during about 5 hours.

A precipitate is formed which is dissolved by the addition of a large volume of ethanol. The product is collected by filtering off the catalyst and concentrating the filtrate. After crystallization, 10 g. of ethyl 4-amino-3-p-chlorophenyl-2-phenyl-butyrate hydrochloride are obtained. Melting point: 272°–274°C. The corresponding base is then isolated by treating the hydrochloride with an equimolecular quantity of sodium hydroxide in water, extracting the resulting aqueous solution with toluene and evaporating the solvent of the extract.

The preparation of ethyl 3-chlorophenyl-3-cyano-2-phenyl-propionate is described in Example 2.

EXAMPLE 2

4-p-chlorophenyl-3-phenyl-2-pyrrolidinone

This example shows a variant of the method described in Example 1 in which the starting material, ethyl 4-amino-3-p-chlorophenyl-2-phenyl-butyrate, is formed in situ and cyclized directly to give 4-p-chlorophenyl-3-phenyl-2-pyrrolidinone.

60 g. of ethyl 3-p-chlorophenyl-3-cyano-2-phenyl-propionate are dissolved in 300 ml. ethanol. The resulting solution is hydrogenated in an autoclave with hydrogen at a pressure of about 100 kg./cm.² using 20 g. of Raney nickel as catalyst. Heating is carried out for about 15 hours at 90°–95°C. After filtration of the catalyst, the filtrate is evaporated to dryness and the residue is recrystallized from toluene. The yield is of the order of 50–60%. The melting point of the resulting 4-p-chlorophenyl-3-phenyl-2-pyrrolidinone varies according to the concentration of the two diastereoisomers. The two cis and trans isomers are prepared by fractional crystallization from toluene and identified by nuclear magnetic resonance analysis. Melting point of the cis isomer: 148°–151°C. Melting point of the trans isomer: 130°–135°C.

The ethyl 3-p-chlorophenyl-3-cyano-2-phenyl-propionate used as starting material is prepared as follows: A mixture of 59 g. of p-chlorophenyl-acetonitrile (0.39 mole), 87.5 g. of ethyl 2-bromo-2-phenyl-acetate (0.36 mole), 150 ml. of toluene and 75 ml. of anhydrous dimethyl-formamide is heated to 60°C. To this there is slowly added a suspension of 0.36 mole of sodium hydride in 50 ml. of toluene, while keeping the temperature at about 60°C. This addition lasts for about 5 hours. Heating is then continued for another 2 hours at 60°–70°C.

The reaction mixture is left to cool, 100 ml. of water are added, neutralization is carried out by the addition of concentrated hydrochloric acid and the organic phase is decanted off. This is concentrated in vacuo and then fractionally distilled in vacuo. The fraction with a boiling point of 180°–190°C./0.1 mm.Hg. (77 g.) is collected and recrystallized from a mixture of 25 ml. of toluene and 150 ml. of petroleum hexane. 62 g. of a product are obtained having a melting point of 72°–86°C.

The following compounds are prepared by the method described in Example 1 or 2; certain physical constants are also given for the esters of the 3-cyano-propionic acids involved in their syntheses:

4-p-chlorophenyl-3-methyl-2-pyrrolidinone

B.P. : 165°–175°C./0.5 mm.Hg.
M.P. : 149°–151°C. (cis isomer)
M.P. : 129°–133°C. (trans isomer)
(separated by fractional crystallization from toluene)
B.P. of ethyl 3-p-chlorophenyl-3-cyano-2-methyl-propionate: 185°C./10 mm.Hg.

4-p-chlorophenyl-3-ethyl-2-pyrrolidinone

B.P. : 160°C./0.2 mm.Hg.
M.P. : 132°–134°C. (cis isomer)
M.P. : 86°–90°C. (trans isomer)
(crystallized from toluene-hexane
B.P. of ethyl 3-p-chlorophenyl-3-cyano-2-ethyl-propionate: 145°–155°C./0.03 mm.Hg.

4-p-chlorophenyl-3,3-dimethyl-2-pyrrolidinone

M.P. : 130°–132°C. (recrystallized from toluene-hexane)
B.P. of ethyl 3-p-chlorophenyl-3-cyano-2,2-dimethyl-propionate: 185°–195°C./13 mm.Hg.

4-o-chlorophenyl-3-phenyl-2-pyrrolidinone

M.P. : 121°–123°C. (recrystallized from toluene)
B.P. of ethyl 3-o-chlorophenyl-3-cyano-2-phenyl-propionate: 180°–190°C./0.03 mm.Hg.

3,4-bis-p-chlorophenyl-2-pyrrolidinone

M.P. : 152°–156°C. (recrystallized from toluene)
B.P. of ethyl 2,3-bis-p-chlorophenyl-3-cyano-propionate: 195°–205°C/0.05 mm.Hg.

3-p-chlorophenyl-4-phenyl-2-pyrrolidinone

M.P. : 95°–108°C. (recrystallized from toluene)
B.P. of ethyl 2-p-chlorophenyl-3-cyano-3-phenyl-propionate: 175°–185°C./0.1 mm.Hg.

4-p-fluorophenyl-3-methyl-2-pyrrolidinone

B.P. : 158°–165°C./0.1 mm.Hg.
M.P. : 90°–118°C. (recrystallized from toluene-hexane)
B.P. of ethyl 3-cyano-3-p-fluorophenyl-2-methyl-propionate: 167°–168°C./10 mm.Hg.

4-m-chlorophenyl-3-phenyl-2-pyrrolidinone

M.P. : 122°–126°C. (recrystallized from absolute ethanol)
B.P. of ethyl 3-m-chlorophenyl-3-cyano-2-phenyl-propionate: 165°–170°C./0.001 mm.Hg.

4-p-fluorophenyl-3-phenyl-2-pyrrolidinone

M.P. : 164°–170°C. (recrystallized from toluene)
B.P. of ethyl 3-cyano-3-p-fluorophenyl-2-phenyl-propionate: 160°–163°C./0.001 mm.Hg.

3-o-chlorophenyl-4-p-chlorophenyl-2-pyrrolidinone

M.P. : 110°–116°C. (recrystallized from toluene-hexane)
B.P. of ethyl 2-o-chlorophenyl-3-p-chlorophenyl-3-cyano-propionate: 170°–180°C./0/25 mm.Hg.

4-m-fluorophenyl-3-phenyl-2-pyrrolidinone

M.P. : 170°–171°C. (recrystallized from ethanol)
B.P. of ethyl 3-cyano-3-m-fluorophenyl-2-phenyl-propionate: 150°–160°C./0.001 mm.Hg.

4-p-chlorophenyl-4-methyl-3-phenyl-2-pyrrolidinone

M.P. : 154°–156°C. (recrystallized from toluene)
M.P. of ethyl 3-p-chlorophenyl-3-cyano-2-phenyl-butyrate: 126°–128°C. (recrystallized from ethanol)

4-o-fluorophenyl-3-phenyl-2-pyrrolidinone

M.P. : 127°–128°C. (recrystallized from toluene)
B.P. of ethyl 3-cyano-3-o-fluorophenyl-2-phenyl-propionate: 145°–155°C/0.001 mm.Hg.

3-phenyl-4-m-trifluoromethylphenyl-2-pyrrolidinone

M.P. : 112°–113°C. (recrystallized from hexane)
B.P. of ethyl 3-cyano-2-phenyl-3-m-trifluoromethyl-phenyl-propionate:
178°–183°C./1 mm.Hg.

4-p-chlorophenyl-4-phenyl-2-pyrrolidinone

M.P. : 145°–146°C. (recrystallized from ethanol)
B.P. of ethyl 3-p-chlorophenyl-3-cyano-3-phenyl-propionate: 170°C./0.2 mm.Hg.

EXAMPLE 3

4p-chlorophenyl-5-methyl-2-pyrrolidinone

This product is obtained by the cyclization of ethyl 4-amino-3-p-chlorophenyl-pentanoate, formed in situ by the catalytic hydrogenation of the corresponding 4-nitro derivative.

50 g. of ethyl 3-p-chlorophenyl-4-nitropentanoate, dissolved in 200 ml. of ethanol, are hydrogenated in an autoclave with hydrogen at a pressure of 100 kg./cm.$^2$, using 10 g. of Raney nickel as catalyst, at a temperature of 100°C. for about 15 hours.

After the reaction has finished, the catalyst is filtered off, the solvent is evaporated and the residue subjected to fractional distillation under vacuum.

Yield: 40%; B.P.: 172°–178°C./0.1 mm.Hg.; M.P.: 114°–120°C. (after recrystallization from toluene-hexane (1:1)).

The ethyl 3-p-chlorophenyl-4-nitro-pentanoate is prepared by the method described by J. Colonge and J. M. Pouchol (Bull.Soc.Chim.Fr. 1962,596–8).

A mixture of 150 g. (2 mole) of nitroethane, 105 g. (0.5 mole) of ethyl-p-chlorocinnamate and 6.6 g. of Triton B (a 35% solution of trimethyl-benzyl-ammonium hydroxide in methanol) is heated for 20 hours at 80°C. After the reaction has finished, toluene is added, washing is carried out with a saturated solution of sodium chloride and the organic solution is dried and evaporated to dryness and the residue is distilled. Yield: 80%; B.P.: 150°–155°C./0.3 mm.Hg.

The following compounds were prepared by the same method:

4-p-chlorophenyl-5,5-dimethyl-2-pyrrolidinone

B.P. : 175°–185°C./0.001 mm.Hg.
M.P. : 151°–154°C. (recrystallized from ethyl acetate).

The ethyl 3-p-chlorophenyl-4-methyl-nitropentanoate used for this synthesis is obtained from 2-nitropropane, ethyl p-chloro-cinnamate and Triton B.
B.P. : 160°–170°C./0.6 mm.Hg.

4-p-chlorophenyl-5-ethyl-3-phenyl-2-pyrrolidinone

M.P. : 133°–138°C. (recrystallized from toluene)
The ethyl 3-p-chlorophenyl-4-nitro-2-phenyl-hexanoate used in this preparation was itself obtained by reaction of 1-p-chloro-phenyl-2-nitro-1-butene with the sodium derivative of ethyl phenylacetate.
M.P. : 118°–120°C. (recrystallized from ethanol).

EXAMPLE 4

3-allyl-3-p-chlorophenyl-2-pyrrolidinone

This product is obtained by the cyclization of ethyl 2-allyl-4-amino-2-p-chlorophenyl-butyrate, formed in situ by the reaction of ethylenimine with the sodium derivative of ethyl 2-allyl-2-p-chlorophenyl-acetate.

To a suspension of 12 g. (0.5 mole) of sodium hydride in 100 ml. of dimethylformamide, there is added rapidly, at a temperature of about 50°C., 0.25 mole of ethyl 2-allyl-2-p-chlorophenyl-acetate (B.P.: 95°–96°C./0.01 mm.Hg.) After th sodium derivative is formed, the reaction mixture is cooled to about −50°C. and there is added to it 11 g. of ethylenimine (0.25 mole) dissolved in 100 ml. of dimethylformamide. The mixture is allowed to return to ambient temperature, an exothermic reaction taking place (internal temperature about 27°C. for a bath temperature around 17°C.). This internal temperature is maintained for about 2 hours, after which heating is carried out at about 65°–70°C. for 1 hour to complete the reaction.

After cooling, 400 ml. of water are added to the mixture which is then extracted with toluene. The toluene extract is washed with a little normal hydrochloric acid and then with water, whereafter it is dried over anhydrous sodium sulfate. It is then evaporated in vacuo and the residue is crystallized from a mixture of ethyl acetate-hexane (1:3).

In this way, 25.4 g. of 3-allyl-3-p-chlorophenyl-2-pyrrolidinone are obtained. M.P. : 101°–102°C.

As a variation of this method, it is also possible to introduce the sodium derivative of the ethyl 2-allyl-2-p-chlorophenyl acetate into a cold solution of ethylenimine in dimethylformamide without the yield and quality of the resulting product being affected.

3-allyl-3-p-chlorophenyl-5-phenyl-2-pyrrolidinone

This compound was obtained as follows:

To a solution of 47.7 g. (0.2 mole) of ethyl 2-p-chlorophenyl-4-pentenoate in 200 ml. of anhydrous dimethylformamide, there is added simultaneously by means of two dropping funnels 7.32 g. (0.2 mole) of a suspension of sodium hydride in anhydrous ethyl ether and 23.8 g. (0.2 mole) of 2-phenyl-ethylenimine, the additions being regulated as a function of the evolution of hydrogen and the temperature being kept below 25°C. The mixture is then heated for one hour at 40°C., then, while stirring vigorously, the reaction is left to continue for 12 hours at ambient temperature.

50 ml. of toluene are added and the solution is then treated several times with water. The organic phase is decanted and dried. By concentration and fractional recrystallization, 20 g. of 3-allyl-3-p-chlorophenyl-5-phenyl-2-pyrrolidinone are separated. M.P. : 197°–198°C. (recrystallized from ethanol). By distillation of the mother liquor at 190°–200°C. under 0.1 mm.Hg. pressure and recrystallization of the distillate from a mixture of hexane-toluene (1:1), about 10 g. of a diastereoisomer are separated. M.P. : 116°–122°C.

These two diastereoisomers have different UV, IR and NMR spectra but their mass spectra are identical. However, it has not been possible to attribute a relative configuration to them.

EXAMPLE 5

3-methyl-4-p-nitrophenyl-2-pyrrolidinone

A mixture of 116 g. of 3-methyl-4-phenyl-2-pyrrolidinone in 330 g. of concentrated sulfuric acid is cooled to about 0°–5°C. Nitration thereof is carried out by adding to it progressively, while maintaining the same temperature, a mixture of 62 g. of fuming nitric acid and 62 g. of concentrated sulfuric acid. The reaction mixture is then stirred for 3 hours, after which it is poured into a mixture of 4 kg. of water and ice. Stirring is continued for another 30 minutes and then the precipitate is filtered off and washed several times with water.

The separated product is recrystallized twice from boiling absolute ethanol.

60 g. of 3-methyl-4-p-nitrophenyl-2-pyrrolidinone are obtained. M.P. : 236°–237°C.

EXAMPLE 6

4-p-aminophenyl-3-methyl-2-pyrrolidinone 45 g. of the 3-methyl-4-p-nitrophenyl-2-pyrrolidinone prepared in Example 5 are dissolved in 3 liters of absolute ethanol and hydrogenated at 100°C. with hydrogen at a pressure of 90 kg./cm.$^2$, in the presence of 5 g. of Raney nickel as catalyst. When the hydrogen absorption has finished, the catalyst is filtered off and the filtrate is evaporated to dryness. The residue is recrystallized twice from ethanol. 30 g. of 4-p-aminophenyl-3-methyl-2-pyrrolidinone are obtained. M.P. : 190°–194°C.

EXAMPLE 7

4-p-bromophenyl-3-methyl-2-pyrrolidinone 13 g. (0.0684 mole) of the 4-p-aminophenyl-3-methyl-2-pyrrolidinone prepared in Example 6, in 40 ml. of 40% hydrobromic acid (0.2236 mole), are cooled to 0°C. Diazotization is carried out by adding, at about 0°–5°C., in small amounts, a solution of 6.1 g. of sodium nitrate in 20 ml. of water. 1 g. of electrolytic copper is then added carefully and the mixture is then heated to 80°C. for 30 minutes. After cooling, the reaction mixture is extracted with toluene and the toluene phase is dried and evaporated to dryness.

The residue is recrystallized from toluene-hexane (1:1).

5 g. of 4-p-bromophenyl-3-methyl-2-pyrrolidinone are obtained. M.P. : 127°–130°C.

EXAMPLE 8

4-p-chlorophenyl-N-methyl-3-phenyl-2-pyrrolidinone

A suspension of 0.115 mole of sodium hydride in toluene is added slowly, keeping the temperature between 30° and 40°C., to a solution of 27.15 g. (0.1 mole) of 4-p-chlorophenyl-3-phenyl-2-pyrrolidinone (mixture of the cis and trans isomers mentioned in Example 2) in a mixture of 70 ml. of toluene and 35 ml. of dimethylformamide. The mixture is stirred for 30 minutes at 40°C.

To this there is then added very slowly 22.7 g. (0.16 mole) of methyl iodide, keeping the temperature at about 40°C. After the addition, the temperature is kept for a further 3 hours at 40°C.

The solvents are evaporated in vacuo and the residue is taken up with toluene. The toluene solution is washed twice with water, dried and concentrated in vacuo.

The residue is recrystallized twice from toluene-hexane (1:1).

19.7 g. of 4-p-chlorophenyl-N-methyl-3-phenyl-2-pyrrolidinone are obtained. M.P. : 111°–112.5°C.

The following compounds are prepared by the same method:

4-p-chlorophenyl-N-methyl-3-methyl-2-pyrrolidinone

B.P. : 140°C./0.1 mm.Hg. Yield: 87%.

N-allyl-4-p-chlorophenyl-3-phenyl-2-pyrrolidinone

B.P. : 200°–204°C./0.001 mm.Hg.

N-n-butyl-4-p-chlorophenyl-3-phenyl-2-pyrrolidinone

B.P. : 204°–206°C./0.001 mm.Hg.

4-p-chlorophenyl-N-n-hexyl-3-phenyl-2-pyrrolidinone

B.P. : 206°–208°C./0.001 mm.Hg.

By the same method, by reacting 4-p-chlorophenyl-3-phenyl-2-pyrrolidinone respectively with 3-bromo-propyne, bromo-cyclopentane and benzyl chloride, there are obtained:

4-p-chlorophenyl-3-phenyl-N-(2-propynyl)-2-pyrrolidinone

Oil purified by chromatography on silica.

Analysis for $C_{19}H_{16}ClNO$: calculated : C, 73.7% H, 5.2% N, 4.52% Cl 11.5%. found : C, 73.1% H, 5.1% N, 4.50% Cl, 11.3%.

4-p-chlorophenyl-N-cyclopentyl-3-phenyl-2-pyrrolidinone

M.P. : 102°–105°C. (recrystallized from toluene-hexane, then ethanol).

N-benzyl-4-p-chlorophenyl-3-phenyl-2-pyrrolidinone

Oil purified by chromatography on silica.

Analysis for $C_{23}H_{20}ClNO$: calculated : C, 76.4% H, 5.52% N, 3.90% Cl 9.82%. found : C, 76.4% H, 5.50% N, 3.80% Cl, 9.20%.

4-p-chlorophenyl-5-phenyl-2-pyrrolidinone 12 g. of 3-carboxy-4-p-chlorophenyl-5-phenyl-2-pyrrolidinone in 200 ml. of xylene are refluxed until evolution of $CO_2$ ceased (about 20 minutes). The solution is cooled, 200 ml. of hexane are added and the reaction product crystallizes out. 8 g. of 4-p-chlorophenyl-5-phenyl-2-pyrrolidinone are obtained. M.P. : 159°–160°C.

The 3-carboxy-4-p-chlorophenyl-5-phenyl-2-pyrrolidinone (after recrystallization from ethanol M.P. : 184°C. (decomposition)) was prepared by condensing 1-p-chlorophenyl-2-nitro-2-phenyl-ethylene with the sodium derivative of diethyl malonate, reduction of the obtained ethyl 2-carbethoxy-3-p-chlorophenyl-4-nitro-4-phenyl-butanoate (M.P. : 148°–149°C. (recrystallized from ethanol) by means of hydrogen under pressure in presence of Raney cobalt and hydrolysis of the resulting 3-carbethoxy-4-p-chlorophenyl-5-phenyl-2-pyrrolidinone (M.P. : 198°C. (recrystallized from toluene)).

We claim:

1. A compound selected from the group consisting of 4-p-chlorophenyl-3-ethyl-2-pyrrolidinone, 4-p-chlorophenyl-3-methyl-2-pyrrolidinone, 4-p-chlorophenyl-3-phenyl-2-pyrrolidinone, 4-o-chlorophenyl-3-phenyl-2-pyrrolidinone, 4-p-fluorophenyl-3-methyl-2pyrrolidinone, 4-p-chlorophenyl-N- methyl-3-phenyl-2-pyrrolidinone, 4-p-fluorophenyl-3-phenyl-2-pyrrolidinone, 3-o-chlorophenyl-4-p-chlorophenyl-2-pyrrolidinone, 4-p-chlorophenyl-4-phenyl-2-pyrrolidinone, N-benzyl-4-p-chlorophenyl-3-phenyl-2-pyrrolidinone, 4-p-chlorophenyl-5-ethyl-3-phenyl-2-pyrrolidinone, 4-p-chlorophenyl-3-phenyl-N-(2-propynyl)-2-pyrrolidinone, 4-p-chlorophenyl-N-cyclopentyl-3-phenyl-2-pyrrolidinone, 3-allyl-3-p-chlorophenyl-5-phenyl-2-pyrrolidinone, 3-phenyl-4-m-trifluoromethylphenyl-2-pyrrolidinone, 4-p-chlorophenyl-3,3-dimethyl-2-pyrrolidinone, 3,4-bis-p-chlorophenyl-2-pyrrolidinone, 3-p-chlorophenyl-4-phenyl-2-pyrrolidinone, 4-m-chlorophenyl-3-phenyl-2-pyrrolidinone, 4-m-fluorophenyl-3-phenyl-2-pyrrolidinone, 4-p-chlorophenyl-4-methyl-3-phenyl-2-pyrrolidinone, 4-o-fluorophenyl-3-phenyl-2-pyrrolidinone, 4-p-chlorophenyl-5-methyl-2-pyrrolidinone, 4-p-chlorophenyl-5,5-dimethyl-2-pyrrolidinone, 3-allyl-3-p-chlorophenyl-2-pyrrolidinone, 3-methyl-4-p-nitrophenyl-2-pyrrolidinone, 4-p-aminophenyl-3-methyl-2-pyrrolidinone, 4-p-bromophenyl-3-methyl-2-pyrrolidinone, 4-p-chlorophenyl-N-methyl-3-methyl-2-pyrrolidinone, N-allyl-4-p-chlorophenyl-3-phenyl-2-pyrrolidinone, N-n-butyl-4-p-chlorophenyl-3-phenyl-2-pyrrolidinone, 4-p-chlorophenyl-N-n-hexyl-3-phenyl-2-pyrrolidinone and 4-p-chlorophenyl-5-phenyl-2-pyrrolidinone.

2. The compound according to claim 1, namely the cis diastereoisomer of 4-p-chlorophenyl-3-phenyl-2-pyrrolidinone.

3. The compound according to claim 1, namely the trans diastereoisomer of 4-p-chlorophenyl-3-phenyl-2-pyrrolidinone.

4. The compound according to claim 1, namely the cis diastereoisomer of 4-p-chlorophenyl-3-methyl-2-pyrrolidinone.

5. The compound according to claim 1, namely the trans diastereoisomer of 4-p-chlorophenyl-3-methyl-2-pyrrolidinone.

6. The compound according to claim 1, namely the 4-p-chlorophenyl-N-methyl-3-phenyl-2-pyrrolidinone.

7. The compound according to claim 1, namely the 4-p-fluorophenyl-3-phenyl-2-pyrrolidinone.

8. The compound according to claim 1, namely the 4-m-chlorophenyl-3-phenyl-2-pyrrolidinone.

9. The compound according to claim 1, namely the 3-o-chlorophenyl-4-p-chlorophenyl-2-pyrrolidinone.

10. The compound according to claim 1, namely the trans diastereoisomer of 4-p-chlorophenyl-3-ethyl-2-pyrrolidinone.

11. The compound according to claim 1, namely 3-phenyl-4-m-trifluoromethylphenyl-2-pyrrolidinone.

* * * * *